United States Patent
Schumacher et al.

(10) Patent No.: US 7,416,600 B2
(45) Date of Patent: Aug. 26, 2008

(54) SILICON-TITANIUM MIXED OXIDE POWDER PRODUCED BY FLAME HYDROLYSIS

(75) Inventors: Kai Schumacher, Hofheim (DE); Martin Moerters, Rheinfelden (DE); Uwe Diener, Grosskrotzenburg (DE); Oswin Klotz, Westerngrund (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 11/568,860

(22) PCT Filed: Apr. 21, 2005

(86) PCT No.: PCT/EP2005/004256

§ 371 (c)(1), (2), (4) Date: Nov. 9, 2006

(87) PCT Pub. No.: WO2005/110922

PCT Pub. Date: Nov. 24, 2005

(65) Prior Publication Data

US 2007/0186816 A1 Aug. 16, 2007

(30) Foreign Application Priority Data

May 18, 2004 (DE) .................. 10 2004 024 500

(51) Int. Cl.
- C09C 1/00 (2006.01)
- C09C 1/28 (2006.01)
- C09C 1/36 (2006.01)
- C01B 13/02 (2006.01)
- B01J 21/06 (2006.01)
- C01G 23/00 (2006.01)
- G03G 9/09 (2006.01)

(52) U.S. Cl. .......................... 106/446; 106/437; 106/445; 423/326; 423/610; 423/611; 423/612; 423/613; 424/59; 424/401; 427/216; 427/220; 428/405; 502/242; 524/443

(58) Field of Classification Search ................ 106/437, 106/445, 446; 423/326, 610, 611, 612, 613; 424/59, 401; 427/216, 220; 428/405; 430/108.6; 205/242; 524/443
See application file for complete search history.

(56) References Cited

U.S. PATENT DOCUMENTS

| | | | |
|---|---|---|---|
| 5,451,390 A * | 9/1995 | Hartmann et al. | 423/610 |
| 5,650,130 A | 7/1997 | Katz et al. | |
| 6,022,404 A * | 2/2000 | Ettlinger et al. | 106/404 |
| 6,773,697 B2 * | 8/2004 | Hemme et al. | 424/65 |
| 6,849,114 B2 * | 2/2005 | Oswald et al. | 106/286.4 |
| 7,083,769 B2 * | 8/2006 | Moerters et al. | 423/326 |
| 7,132,157 B2 * | 11/2006 | Oswald et al. | 428/325 |
| 2003/0129153 A1 | 7/2003 | Moerters et al. | |
| 2003/0232149 A1 * | 12/2003 | Oswald et al. | 427/453 |
| 2004/0034144 A1 | 2/2004 | Scharfe et al. | |
| 2006/0057385 A1 * | 3/2006 | Schumacher et al. | 428/404 |

FOREIGN PATENT DOCUMENTS

EP 0 722 992 7/1996

OTHER PUBLICATIONS

U.S. Appl. No. 11/569,415, filed Nov. 20, 2006, Schumacher, et al.
U.S. Appl. No. 11/568,860, filed Nov. 9, 2006, Schumacher, et al.
U.S. Appl. No. 11/722,782, filed Jun. 25, 2007, Schumacher, et al.

* cited by examiner

*Primary Examiner*—Anthony J Green
(74) *Attorney, Agent, or Firm*—Oblon, Spivak, McClelland, Maier & Neustadt, P.C.

(57) ABSTRACT

Silicon-titanium mixed oxide powder produced by flame hydrolysis, which consists of aggregates of primary particles, with a BET surface area of 90±15 $m^2/g$, a titanium dioxide proportion of 50±8 wt. % and an anatase/rutile ratio of 60:40 to 70:30.

It is produced in that a mixture of silicon halide, titanium halide, hydrogen and primary air is ignited in a burner and the flame is burned into a reaction chamber closed off from the surrounding air, and secondary air and a gas, which increases the temperature in the reaction chamber by combustion and/or which slows down the cooling in the reaction chamber because of low heat transfer, are additionally introduced into the reaction chamber.

It can be used in toner compositions.

13 Claims, No Drawings

SILICON-TITANIUM MIXED OXIDE POWDER PRODUCED BY FLAME HYDROLYSIS

The present invention relates to a silicon-titanium mixed oxide powder produced by flame hydrolysis and to the production and use thereof.

U.S. Pat. No. 6,677,095 discloses the use of binary metal mixed oxide powders with the components silicon dioxide, aluminium oxide and titanium dioxide, preferably in hydrophobised form. These powders are said to have good dispersibility, good flow properties and a high electrostatic charge.

From EP-A-722992, surface-modified metal mixed oxide powders, e.g. silicon-titanium mixed oxide powder, and their use as a charge stabiliser and anti-caking agent in toner powders are known. However, it has been found that no suitable toner compositions can generally be obtained with the hydrophobised powders disclosed in EP-A-722992.

In U.S. Pat. No. 6,130,020, composites of the composition $Si_xTi_yO_{(4x+yz)/2}$ are claimed for use in toner compositions. In this formula, z is the valency of titanium and x/y is 1 to 25. Within the range specified by the quotient x/y, all compositions are equally suitable for toner applications. U.S. Pat. No. 6,130,020 discloses nothing about the modification of the oxides, their BET surface area or their composition.

It is known to produce silicon-titanium mixed oxide powder by flame hydrolysis. In this process, a mixture of silicon tetrachloride and titanium tetrachloride is generally hydrolysed in a flame. The flame can be produced e.g. by reacting hydrogen and atmospheric oxygen. As a result, the water necessary for the hydrolysis of the chlorides is formed. As reaction products, the silicon-titanium mixed oxide powder and hydrochloric acid are obtained, some of which remains adhering to the powder.

In the processes described in the prior art, however, only powders with a limited $TiO_2/SiO_2$ ratio are formed.

Thus, in DE-A-2931810, a silicon-titanium mixed oxide powder is claimed, which contains 0.1 to 9.9 wt. % titanium dioxide. It is produced in that silicon tetrachloride is evaporated, diluted with pre-heated air and mixed with hydrogen and titanium tetrachloride in a mixing chamber and the mixture is burned in a reaction chamber.

In DE-A-4235996, a silicon-titanium mixed oxide powder is claimed which contains 70 to 99 wt. % titanium dioxide. It is produced in that silicon tetrachloride is evaporated and transferred into a mixing chamber by means of an inert gas, mixed therewith hydrogen, air and titanium tetrachloride and the mixture is burned in a reaction chamber.

The mixed oxide powders or hydrophobised mixed oxide powders described hitherto are unsuitable, or of only limited suitability, for use in a toner composition.

The object of the invention is therefore to provide a silicon-titanium mixed oxide powder that can be used particularly advantageously in toner compositions. It should exhibit advantages over the prior art in terms of dispersibility, flowability and electrostatic charge.

The invention also provides a process for the production of these silicon-titanium mixed oxide powders.

The invention also provides a silicon-titanium mixed oxide powder produced by flame hydrolysis, which consists of aggregates of primary particles and is characterised in that the BET surface area is 90±15 m²/g, the titanium dioxide portion is 50±8 wt. % and the anatase/rutile ratio is 60:40 to 70:30.

The term flame hydrolysis refers to processes in which an evaporated metal precursor or metalloid precursor is hydrolysed in the presence of a flame. The flame is produced by the reaction of hydrogen, methane or similar gases with air or oxygen. At least one reaction product is water, which brings about the hydrolysis of the metal precursor or metalloid precursor. As a result, primary particles are initially formed, which fuse together into aggregates during the reaction.

In the mixed oxide powder according to the invention, crystalline titanium dioxide is present, while the silicon dioxide portion is X-ray amorphous. TEM photographs of aggregates show, among other things, primary particles with a partial or complete silicon dioxide shell and a titanium dioxide core. In addition, there are primary particles in which silicon dioxide and titanium dioxide are present together, and which have a Ti—O—Si bond.

It has been shown that a powder with such a composition, BET surface area and anatase/rutile ratio is ideally suited for use in toner compositions. In these, it displays good dispersibility, high flowability and a high electrostatic charge.

In addition to $SiO_2$ and $TiO_2$, the mixed oxide powder according to the invention can also contain small quantities of impurities from the feed materials or process-related impurities. In total, these impurities are less than 1 wt. %, generally less than 0.1 wt. %. In particular, the mixed oxide powder according to the invention can also contain chloride.

Mixed oxide powders according to the invention with a number-based median value of the primary particle diameters of 14 to 18 nm and a number-based 90% span of the primary particle diameters of 5 to 40 nm can be preferred. The narrow primary particle distribution can display further advantages in toner application and in catalytic applications.

In addition to the primary particles, the aggregate sizes can also be varied. In particular, a mixed oxide powder according to the invention having number-based median values:
 of the equivalent circle diameter (ECD) of less than 95 nm,
 of the aggregate area of less than 7500 nm² and
 of the aggregate circumference of less than 600 nm can be advantageous here.

Furthermore, the tamped density of the mixed oxide powder according to the invention can be varied. The tamped density can play an important part in the metering and processing of the powder. It is generally between 20 and 200 g/l. The mixed oxide powder according to the invention can preferably have a tamped density of 40 to 80 g/l.

The invention also provides a process for the production of the silicon-titanium mixed oxide powder according to the invention, in which
 a silicon halide and a titanium halide are evaporated,
 the vapours are transferred into a mixing chamber by means of a carrier gas,
 separately from this, hydrogen and primary air, which can optionally be enriched with oxygen and/or preheated, are transferred into the mixing chamber,
 and then the mixture of silicon halide, titanium halide, hydrogen and primary air is ignited in a burner and the flame is burned into a reaction chamber closed off from the surrounding air, and
 in addition, separately from one another, secondary air and a gas or a gas mixture which increases the temperature in the reaction chamber by combustion, and/or
  which, because of low heat transfer, slows down the cooling in the reaction chamber,
 are introduced into the reaction chamber, preferably via an annular nozzle,
 and then the solid is separated from gaseous substances, and
 the solid is subsequently freed from halide-containing substances, to the greatest possible extent, by a treatment with steam at temperatures of 250 to 700° C.

It is essential in the process according to the invention that a gas or a gas mixture is introduced which increases the temperature in the reaction chamber by combustion and/or which slows down the cooling in the reaction chamber because of low heat transfer. With this measure, it is possible to obtain a powder that achieves the values claimed with respect to $SiO_2/TiO_2$ content, BET surface area and anatase/rutile content.

As a gas that increases the temperature in the reaction chamber by combustion, preferably hydrogen, methane, ethane, propane or natural gas can be used.

As a gas that slows down the cooling in the reaction chamber because of a low heat transfer, helium, argon, carbon dioxide and/or carbon monoxide can be used.

Both types of gases are preferably used in a quantity of 0.0005 to 5 $Nm^3/h$ per kilogram/hour $SiCl_4$. A range of 0.001 to 1 $Nm^3/h$ per kilogram/hour $SiCl_4$ can be particularly preferred.

As silicon halides, silicon tetrachloride, methyl-trichlorosilane and/or trichlorosilane can preferably be used, silicon tetrachloride being particularly preferred. As titanium halide, titanium tetrachloride can preferably be used.

It has also proved advantageous to keep the evaporation temperature of titanium halide and silicon halide as low as possible. In the case of titanium tetrachloride, or titanium and silicon tetrachloride if these are evaporated as a mixture, it is advantageous if the evaporation temperature is no higher than 180° C. In the case of silicon tetrachloride, it is favourable if the evaporation temperature is no higher than 100° C. These measures can increase the purity of the product.

The ratio of hydrogen feed to the amount required stoichiometrically is referred to as gamma. Similarly, the ratio of oxygen feed to the oxygen required stoichiometrically is referred to as lambda. The term 'required stoichiometrically' here means the precise quantity of hydrogen and oxygen respectively required for the hydrolysis of the titanium-silicon halide. The following thus applies:

Gamma=$H_2$ feed (mol)/$H_2$ stoichiometric (mol)

Lambda=$O_2$ feed (mol)/$O_2$ stoichiometric (mol)

In the process according to the invention, it has proved advantageous if gamma and lambda are greater than 1.05.

Furthermore, in the process according to the invention, in addition to the primary air in the mixing chamber, air is introduced directly into the reaction chamber (secondary air). It has been shown that, without feeding the additional air into the mixing chamber, no mixed oxide powder according to the invention can be obtained. It can be advantageous here if the primary air/secondary air ratio is between 10 and 0.5.

To be able to meter the quantity of secondary air and gases being introduced into the reaction chamber accurately, the flame is allowed to burn into a reaction chamber closed off from the surrounding air. This enables precise process control to be achieved. The vacuum prevailing in the reaction chamber is preferably between 5 and 80 mbar.

The outlet velocity of the reaction mixture from the burner into the reaction chamber can preferably be 10 to 80 m/s.

The invention also provides a process for the production of a hydrophobised silicon-titanium mixed oxide powder by spraying the silicon-titanium mixed oxide powder produced by flame hydrolysis according to the invention with a water repellent or a mixture of water repellents, optionally in the presence of water, subsequently mixing for 15 to 30 minutes and then tempering over a period of 1 to 6 hours at a temperature of 100 to 500° C.

All the water repellents listed in EP-A-722992 can be used for this purpose, hexamethyldisilazane, trimethoxyoctylsilane, dimethylpolysiloxane and trimethoxypropylsilane being preferred.

The invention also provides a hydrophobised silicon-titanium mixed oxide powder produced by this process.

The hydrophobised silicon-titanium mixed oxide powder can have a BET surface area of 50 to 100 $m^2/g$ and a carbon content of 0.5 to 5 wt. %, depending on the reaction conditions.

The invention also provides the use of the silicon-titanium mixed oxide powder according to the invention and the hydrophobised silicon-titanium mixed oxide powder according to the invention in toner mixtures, as a UV blocker in cosmetic preparations, as a catalyst or catalyst support, as a photocatalyst, as a reinforcing filler in silicone rubber and rubber, as an anti-caking agent, as an anti-blocking agent in films and as a thickener in paints.

EXAMPLES

Analysis

The BET surface area is determined in accordance with DIN 66131. The content of $SiO_2$ and $TiO_2$ is determined by X-ray fluorescence analysis and/or chemical analysis. The tamped density is determined with reference to DIN ISO 787/XI K 5101/18 (unsieved). The pH value is determined with reference to DIN ISO 787/IX, ASTM D 1280, JIS K 5101/24.

The primary particle and aggregate sizes are determined by image analysis. The image analyses are performed using a TEM instrument from Hitachi H 7500 and a MegaView II CCD camera from SIS. The image enlargement for the evaluation is 30000:1 with a pixel density of 3.2 nm. The number of particles evaluated is greater than 1000. The preparation takes place according to ASTM3849-89. The lower threshold limit with respect to detection is 50 pixels.

xamples 1 to 4

Silicon tetrachloride and titanium tetrachloride are evaporated together in an evaporator at 160° C. The vapours are transferred into a mixing chamber by means of nitrogen. Separately from this, hydrogen and primary air are introduced into the mixing chamber. In a central pipe, the reaction mixture is fed to a burner and ignited. The flame burns into a water-cooled flame tube. In addition, separately from one another, secondary air and hydrogen or carbon dioxide or a mixture of hydrogen and carbon dioxide are introduced into the reaction chamber. The resulting powder is separated off in a downstream filter and then treated with steam in countercurrent.

Feed materials and quantities as well as flame parameters are given in Table 1. The physico-chemical data of the powders are given in Table 2.

Example 5

Hydrophobising of the Mixed Oxide Powder from Example 2

The mixed oxide powder from Example 2 is sprayed with 10 g dimethylpolysiloxane/100 g mixed oxide powder and subsequently mixed for 20 minutes. Tempering is then performed over a period of 2 hours at a temperature of 250° C.

The product has a BET surface area of 74 m$^2$/g and a carbon content of 2.5%.

Example 6 is carried out in the same way as Example 5, but with a mixed oxide powder produced in accordance with DE-A-2931810 with 91 wt. % SiO$_2$ and 9 wt. % TiO$_2$. BET surface area and carbon content are comparable with those from Example 5.

Example 7 is carried out in the same way as Example 5, but with a mixed oxide powder produced in accordance with DE-A-4236996 with 25 wt. % SiO$_2$ and 75 wt. % TiO$_2$. BET surface area and carbon content are comparable with those from Example 5.

Examples 8-10

Toner compositions containing the mixed oxide powder according to the invention from Example 5, 6 or 7 are produced in accordance with U.S. Pat. No. 6,130,020, column 6, lines 61 ff.

Table 3 shows the advantages of a toner composition when the hydrophobised mixed oxide powder from Example 5 according to the invention is used. Table 1: Feed materials and flame parameters

TABLE 3

Properties of toner mixtures

| Powder from example | SiO$_2$/TiO$_2$ | Charge properties | Incorporability | Dispersibility |
|---|---|---|---|---|
| 5 | 50/50 | + | + | + |
| 6 | 91/9 | + | − | − |
| 7 | 25/75 | ○ | + | ○ |

The invention claimed is:

1. Silicon-titanium mixed oxide powder produced by flame hydrolysis, consisting of aggregates of primary particles, wherein
   a BET surface area is 90±15 m$^2$/g,
   a proportion of titanium dioxide is 50±8 wt. %, and
   an anatase/rutile ratio is 60:40 to 70:30.

2. The silicon-titanium mixed oxide powder produced by flame hydrolysis according to claim 1, wherein a number-based median value of the primary particle diameters is 14 to 18 nm and a number-based 90% span of the primary particle diameters is 5 to 40 nm.

3. The silicon-titanium mixed oxide powder produced by flame hydrolysis according to claim 1, wherein a number-based median value
   of an equivalent circle diameter of the aggregates (ECD) is less than 95 nm,
   of an aggregate area is less than 7500 nm$^2$ and
   of an aggregate circumference is less than 600 nm.

| | | | Burner | | | | | Reaction chamber | | |
|---|---|---|---|---|---|---|---|---|---|---|
| Example | SiCl$_4$ kg/h | TiCl$_4$ kg/h | H$_2$ Nm$^3$/h | Air primary Nm$^3$/h | $v_{Br}$$^{(\S)}$ m/s | Gamma | Lambda | Air sec. Nm$^3$/h | CO$_2$ Nm$^3$/h | H$_2$ Nm$^3$/h |
| 1 | 3.60 | 3.00 | 2.50 | 9.70 | 26.9 | 1.51 | 1.61 | 20 | — | 0.8 |
| 2 | 4.00 | 2.70 | 2.50 | 9.60 | 27.5 | 1.48 | 1.61 | 20 | 0.5 | — |
| 3 | 3.60 | 3.00 | 3.30 | 13.30 | 36.9 | 1.99 | 1.69 | 20 | 0.2 | 0.2 |
| 4 | 3.60 | 3.00 | 3.30 | 13.30 | 36.9 | 1.99 | 1.69 | 20 | — | 0.9 |

$^{(\S)}$Velocity of reaction mixture on transfer from burner to reaction chamber

TABLE 2

Physico-chemical data of the silicon-titanium mixed oxide powders

| | | | | | | Primary particles | | | Aggregates(*) | | |
|---|---|---|---|---|---|---|---|---|---|---|---|
| Ex. | BET m$^2$/g | SiO$_2$ wt. % | TiO$_2$ wt. % | Anatase/rutile | pH(&) | Tamped density g/l | Median diameter nm (*) | 90% span nm | Median ECD nm | Median area nm$^2$ | Median circumference nm |
| 1 | 79 | 51.4 | 48.6 | 65/35 | 3.63 | 53 | —$^{(\S)}$ | — | — | — | — |
| 2 | 92 | 55.2 | 44.8 | 66/34 | 3.64 | 49 | 16.1 | 8.5-36.4 | 73.0 | 4183 | 438 |
| 3 | 100 | 49.9 | 51.1 | 64/36 | 3.75 | 48 | 15.8 | 6.4-41.3 | 74.2 | 4225 | 445 |
| 4 | 83 | 50.5 | 49.5 | 61/39 | 3.9 | 51 | — | — | — | — | — |

(*)number-based values
(&)4 percent, aqueous dispersion
$^{(\S)}$— = not determined 4. The silicon-titanium mixed oxide powder produced by flame hydrolysis according to claim 1, wherein a tamped density of the silicon titanium mixed oxide powder is 40 to 80 g/l.

5. A process for the production of the silicon-titanium mixed oxide powder according to claim 1, comprising
evaporating a silicon halide and a titanium halide,
transferring silicon halide and titanium halide vapours formed by the evaporating, into a mixing chamber by means of a carrier gas,
transferring into the mixing chamber, separately from the above steps, hydrogen and primary air, which can optionally be enriched with oxygen and/or preheated,
and then igniting the mixture of silicon halide, titanium halide, hydrogen and primary air in a burner wherein the flame is burned into a reaction chamber closed off from surrounding air, and
in addition, separately from one another, introducing into the reaction chamber secondary air and
a gas or a gas mixture
which increases a temperature in the reaction chamber by combustion, and optionally
slows down a cooling in the reaction chamber,
and then separating a solid from gaseous substances, and
freeing the solid from halide-containing substances, by a treatment with steam at temperatures of 250 to 700° C.

6. The process according to claim 5, wherein the gas or gas mixture that increases the temperature in the reaction chamber by combustion is at least one gas selected from the group of gases consisting of hydrogen, methane, ethane, propane and natural gas.

7. The process according to claim 5, wherein the gas that optionally slows down the cooling in the reaction chamber is at least one gas selected from the group of gases consisting of helium, argon, carbon dioxide and carbon monoxide.

8. The process according to claim 6, wherein the gas or gas mixture that increases the temperature in the reaction chamber by combustion is used in a quantity of 0.0005 to 5 $Nm^3/h$ per kilogram/hour $SiCl_4$.

9. The process according to claim 5, wherein a gamma value and a lambda value are greater than 1.05.

10. A process for the production of a hydrophobised silicon-titanium mixed oxide powder, comprising:
spraying the silicon-titanium mixed oxide powder produced by flame hydrolysis according to claim 1 with a water repellent or a mixture of water repellents, optionally in the presence of water,
subsequently mixing for 15 to 30 minutes and then tempering for a period of 1 to 6 hours at a temperature of 100 to 500° C.

11. The process according to claim 10, wherein the water repellent is at least one water repellent selected from the group of water repellents consisting of hexamethyldisilazane, trimethoxyoctylsilane, dimethylpolysiloxane, and trimethoxypropylsilane.

12. A hydrophobised silicon-titanium mixed oxide powder obtained by the process according to claim 10.

13. A composition comprising the silicon-titanium mixed oxide powder produced by flame hydrolysis according to claim 1 wherein the composition is at least one selected from the group consisting of a toner mixture, a UV blocker in cosmetic preparations, a catalyst or catalyst support, a photocatalyst, a reinforcing filler in silicone rubber and rubber, an anti-caking agent, an anti-blocking agent in films and a thickener in paints.

* * * * *